United States Patent [19]

Stephan

[11] Patent Number: 5,677,535
[45] Date of Patent: Oct. 14, 1997

[54] GAMMA CAMERA WITH APPROACH AND SAFETY PLANES

[75] Inventor: Philippe Stephan, Le Mesnil St. Denis, France

[73] Assignee: Sopha Medical, Buc Cedex, France

[21] Appl. No.: 432,274

[22] Filed: May 1, 1995

[30] Foreign Application Priority Data

May 3, 1994 [FR] France .................. 94 05394

[51] Int. Cl.⁶ ................................... G01T 1/20
[52] U.S. Cl. ................... 250/363.02; 250/363.05
[58] Field of Search ............ 250/363.05, 363.04, 250/363.02; 378/20

[56] References Cited

U.S. PATENT DOCUMENTS

| | | | |
|---|---|---|---|
| 4,943,726 | 7/1990 | Plummer | 250/363.02 |
| 5,319,205 | 6/1994 | Kline et al. | 250/363.02 |
| 5,486,700 | 1/1996 | Silberklang et al. | 250/363.02 |

FOREIGN PATENT DOCUMENTS

| | | |
|---|---|---|
| 0048075 | 3/1982 | European Pat. Off. . |
| 0485707 | 5/1992 | European Pat. Off. . |
| 4344882 | 7/1994 | Germany . |
| 9412894 | 6/1994 | WIPO . |

*Primary Examiner*—David P. Porta
*Assistant Examiner*—Richard Hanig
*Attorney, Agent, or Firm*—Edward J. Kondracki; Kerkam, Stowell, Kondracki & Clarke, P.C.

[57] ABSTRACT

Disclosed is a gamma camera having a base movable on a frame and at least one arm that is movable with respect to said frame and is provided, at one free end, with a plane detector. This camera further comprises two approach planes that are substantially parallel to the plane of said detector so as to servo-control the position of one edge of the patient between these two planes. The invention can be applied especially to gamma cameras that comprise two detectors and are capable of carrying out tomography and full-body examinations.

23 Claims, 2 Drawing Sheets

GAMMA CAMERA WITH APPROACH AND SAFETY PLANES

BACKGROUND OF THE INVENTION

1. Field of the Invention

The present invention relates to the field of gamma cameras and more particularly to the field of gamma cameras having a base movable on a frame and bearing at least one arm provided, at its free end, with a detector head or detector.

This detector generally has a collimator, a scintillator and an array of photomultiplier tubes whose input faces, which are juxtaposed with one another, cover the detection surface of said detector and determine its detection field.

The following is the principle of the examination. A radioactive substance is injected into a patient to be examined. The gamma radiation produced by the radioactive emission that comes out of this patient goes through the collimator and excites the scintillator which converts the energy of the gamma photons into light energy that can be detected by the photomultiplier tubes. These tubes then produce electrical signals that depend on the light intensity received.

By carrying out operations of barycentric localization on all these signals, it is possible to determine the X, Y coordinates of the origin of the scintillation in the field of detection and, by totalizing the number of scintillations detected throughout the field of detection, an image is obtained for a given viewing angle that reveals the distribution of concentration of radioactive substance in the patient's body.

2. Description of the Prior Art

In order to improve the sensitivity of gamma cameras, these cameras were initially made with two detector heads instead of only one. Then, a motor-driven device was made, enabling these heads to be moved away from each other or towards each other in order to approach the patient's body as closely as possible.

However, in order to prevent any collision between the detector heads and the patient, a collision-preventive carpet was placed between the patient and the collimators. This carpet works for example by air pressure and is designed to stop the motions of the detectors of the gamma camera as soon as the patient's body comes into physical contact with said carpet.

This carpet therefore is a safety element, enabling an operator to control the approaching of the detector heads above the patient's body with a certain degree of flexibility. However, such an approach made by estimation is imprecise and, in any case, it can be neither automated nor servo-controlled. In practice, the collimator is often placed, during the examination, at more than five centimeters from the patient's body. Now, at such a distance, the resolution of the gamma camera is considerable lessened.

Hence, the present invention is aimed at proposing a gamma camera that overcomes the above-mentioned drawbacks at low cost and especially makes it possible to obtain a computed and improved approach to the patient, said approach being possibly made automatically in the different relative positions of the detector head with respect to this patient's body, in every type of examination that can be carried out by a gamma camera.

The principle of the invention then consists in setting up two planes of detection. So long as the patient's body does not intersect a first plane, the detector can be made to approach the body. When the body intersects a second plane, the detector is moved away. The aim is that the patient's contour should be located between these two planes.

SUMMARY OF THE INVENTION

This aim, as well as others that shall appear hereinafter, are achieved by means of a gamma camera having a base movable on a frame and bearing at least one arm that is movable with respect to said frame and is provided, at a free end, with a plane detector wherein said camera further comprises two approach planes that are substantially parallel to the plane of said detector so as to servo-control the position of one edge of the patient between the boundaries of these two planes.

According to another aspect of the invention, the approach planes are produced by two linear arrays placed so as to face each other on a detachable frame of the collimator.

BRIEF DESCRIPTION OF THE DRAWINGS

The following description, which is in no way restrictive, shall provide for a clearer understanding of the way in which the invention can be put into practice.

It must be read with reference to the appended drawings, of which.

MORE DETAILED DESCRIPTION

Figure 1:
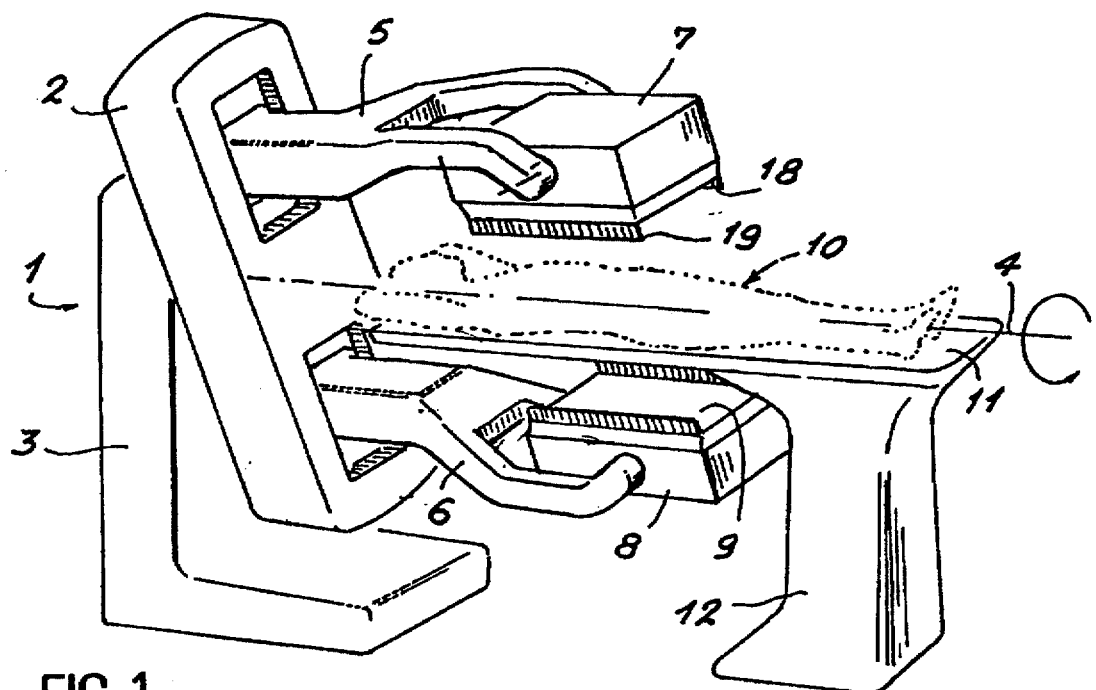
FIG. 1 gives a view in perspective of a gamma camera according to the invention in a so-called 180° tomographic position.

The invention relates to a gamma camera 1 having a base 2 that is movable on a frame 3 so as to rotate about a rotational axis 4 called the axis of the gamma camera. The gamma camera 1 herein has two arms 5, 6 each provided, at its free end, with a detector head or detector 7, 8. The other ends of the arms 5 and 6 are each held in a base 2. The arms may move away radially from the axis 4. Each detector 7, 8 has a collimator 9 whose surface, when it is rectangular, is bounded by two large sides and two small sides. A patient referenced 10 in FIG. 1 is lying on a bed 11 between the detectors 7, 8 for an examination. The bed 11 is borne by a pedestal 12 that can be moved along rails not shown in the figures. Depending on the type of examination required, the bed 11 may be oriented along the axis 4 or else orthogonally to this axis.

For example, in a so-called full-body examination, the bed 11 is positioned orthogonally to the axis 4. The detectors 7, 8 face each other and the gamma camera 1 moves along the bed 11 so that the examination covers the entire body of the patient 10.

On the contrary, in the so-called 180° tomographic examination, the bed 11 is parallel to the axis 4. The detectors 7, 8 face each other and the base 2 rotates about the axis 4 driving the detectors 7, 8 rotationally about the body of the patient 10. This is the position shown in FIG. 1.

Finally, in a so-called 90° tomographic examination, the bed 11 is parallel to the axis 4. However, the detectors 7, 8 are positioned at 90° to each other and the base 2 moves and rotates about the rotational axis 4, driving the detectors 7, 8 in a substantially circular motion about the patient 10.

These two orientations of the bed 11 with respect to the axis 4 are characteristic of gamma cameras that have no tunnel-shaped mount. Indeed, for these cameras, the bed on which the patient lies is inserted into a narrow tunnel that does not permit the patient to be oriented orthogonally to the axis of this tunnel. However, these other gamma cameras may also be provided with planes according to the invention.

Figure 2:
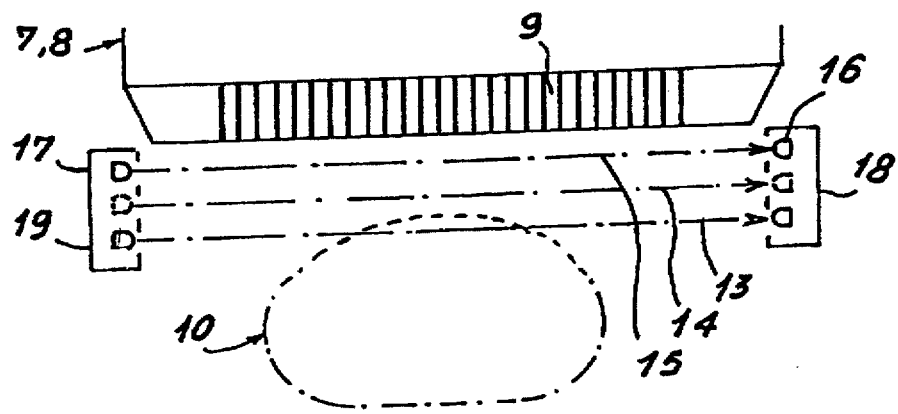
FIG. 2 gives a sectional and schematic view of the principle of operation of the approach and safety planes of a gamma camera according to the invention.

According to the invention, the detectors 7, 8 have several planes of light substantially parallel to the collimator 9. These planes, which cover the entire surface of the collimator 9, are formed for example by infrared light beams. Two of them, referenced 13 and 14 in FIG. 2, form approach planes while a third plane positioned between the collimator 9 and the approach planes 13, 14 form a so-called safety plane 15.

The approach planes 13, 14 are designed to servo-link the position of the detectors 7, 8 in relation to the edge of the patient's body 10 while the safety plane 15 is designed to define a proximity boundary position of the detectors 7, 8 with respect to this patient 10.

When a patient 10 is examined, the detectors 7, 8 are clamped to his body so that the approach plane 13, namely the plane furthest from the collimator 9, is sectioned without this being the case for the approach plane 14. An algorithm such as the one defined here below makes it possible to keep the patient 10 in the boundaries of the planes 13 and 14: "the plane 13 must be cut and the plane 14 cleared; if the plane 14 is cleared, bring the detector 7 or 8 closer; if the plane 14 is cut, move it away". Furthermore, if the moving away of the detector 7 or 8 is not enough to compensate for an excessive variation in the contour of the patient's body 10, the safety plane 15 is cut and the movements of the gamma camera 1 are immediately stopped. This prevents any collision between the patient 10, and the detectors 7, 8. Consequently, the detectors automatically avoid touching the patient 10 under conditions of total safety.

The distance between the planes 13, 14, 15 is less than about one centimeter. Now the safety plane 15 is positioned at less than about one centimeter from the surface of the collimator 9. Hence, the edge of the patient's body 10 remains constantly at less than about three centimeters from the collimator 9.

Each plane 13, 14, 15 is generated by a row or line of fixed light-emitting photodiodes 16 and by a receiver row of photodetectors, for example phototransistors 17, positioned so as to face the above-mentioned row of diodes. The management of emission and reception are done respectively by an electronic emission circuit and an electronic reception circuit.

The ambient light is liable to disturb the reception of infrared rays by the phototransistor 17. Hence, in order to minimize or even eliminate this disturbance, a circuit to compensate for the level of ambient lighting has been placed. Furthermore, it has been sought to increase the emission capacity of the diodes 16. Hence, diodes 16 have been chosen whose emission cone has an angle of about 20°. Furthermore, the emission time of the diodes 16 has been minimized while, at the same time, this emission is synchronized with the reception of the phototransistors 17 by a synchronizer. Thus, only a phototransistor 17 placed so as to be directly facing a light-emitting diode 16 actually receives infrared light. The emitter-receiver synchronization eliminates problems of multiple illumination and multiple reception. Thus, the phototransistors neighboring a selected phototransistor at a given instant receive the light emitted by the photodiode corresponding to this selective phototransistor. However, the signals of these other phototransistors are not taken into account at this time owing to the synchronization circuit which eliminates their contributions. Furthermore, a scanning is done of the emission along different rows of diodes. The emission is then done one diode after another on a first row, then one diode after another on a second row and finally one diode after another on a third row before the cycle starts again on the first row. It is nevertheless possible to put the first diodes of the different rows into operation successively and propagate this emission from one edge of the plane to the other. It is also possible to choose a pseudo-random mode which would be applied in synchronism also on the phototransistors side.

In practice, there are about thirty diodes 16 per row. These diodes 16 are separated from one another by a space of about one centimeter. Since the emission time is about 50 microseconds, within about 10 milliseconds, all the rows forming the planes 13, 14, 15 have been scanned. And, if the diodes 16 are supplied with a current having an intensity substantially equal to 500 mA, the infrared rays are emitted with sufficient power to cross distances of about 70 centimeters without being disturbed by the ambient light. An infrared filter placed between the phototransistors 17 and the above-mentioned compensation circuit increases this immunity.

Furthermore, diodes 26 are advantageously positioned between the rows of phototransistors 17 in order to carry out the direct testing of their efficiency.

Furthermore, on their top, namely beneath the row 13 of diodes or phototransistors, these linear arrays have proximity sensors.

Figure 3:
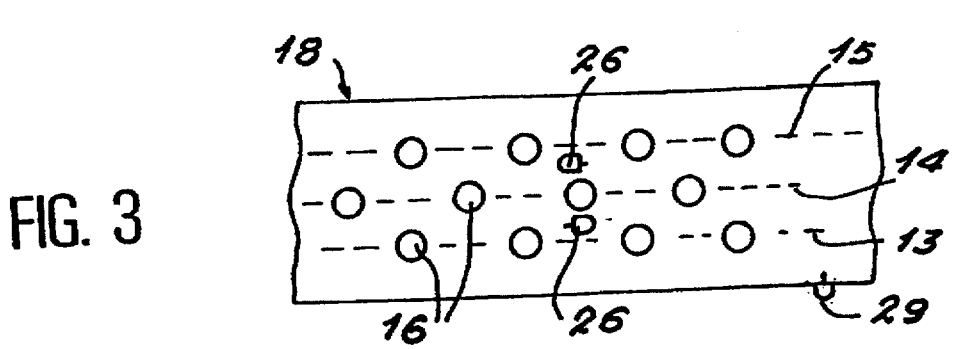
FIG. 3 gives a front view of the quincunxial arrangement of the diodes or phototransistors that are the source of the approach and safety planes of a gamma camera according to the invention.

As shown in FIG. 3, the diodes 16 and the phototransistors 17 are advantageously arranged quincunxially. Thus, a row of diodes 16 of a plane 13, 14, 15 is offset with respect to the perpendicular to the diodes of a row of diodes of a plane that neighbors it. Thus, the number of diodes 16 and phototransistors 17 is limited. At the same time a detection grid is obtained that is narrow enough for an object with a diameter of about one centimeter to be detected at least by one of the planes 13 or 14.

Figure 4:
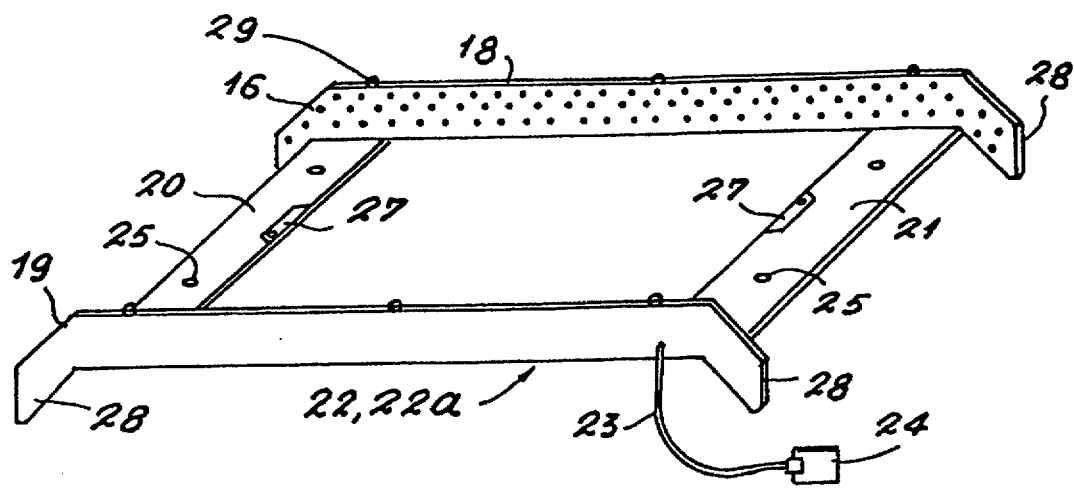
FIG. 4 gives a view in perspective of a detachable frame used for the implementation of the invention.

The planes 13, 14 and 15 are obtained with two linear arrays 18, 19 positioned so as to face each other. These linear arrays 18, 19 are, for example, bonded to the ends of two flat segments 20, 21, the set 18, 19, 20, 21 forming a frame referenced 22 in FIG. 4. The linear arrays 18 and 19 bear the diodes and phototransistors respectively.

A single cable 23 connects the frame 22 to a connector 24. This connector 24 is designed to be connected to a connector of the detector 7, 8. The cable 23 thus makes it possible provide for the electrical supply of the linear arrays 18, 19 as well as for the sending of the activation and detection signals of the phototransistors 17 of the reception array 19 to an electronic card of the gamma camera 1 designed notably to drive its motors.

The linear arrays 18, 19 must be located on either side of the patient 10, to his/her right and left. Thus, the linear arrays 18, 19 will not come into contact with the patient's body 10 during an examination. The linear arrays have ends that are chamfered and, in certain cases curved, close to the plates 20 and 21.

Figure 5:
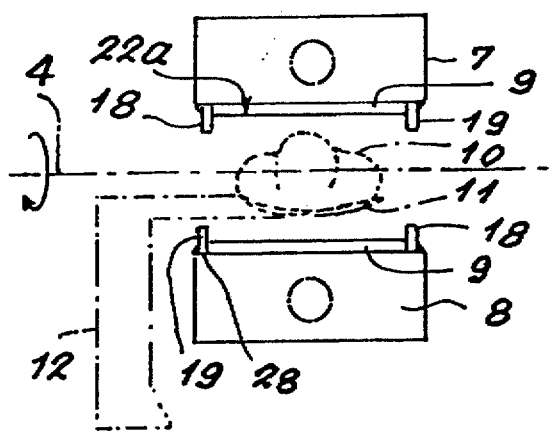
FIGS. 5a, 5b and 5c give a schematic view, in different positions each suited to a particular type of examination, of a gamma camera according to the invention.
Figure 5:
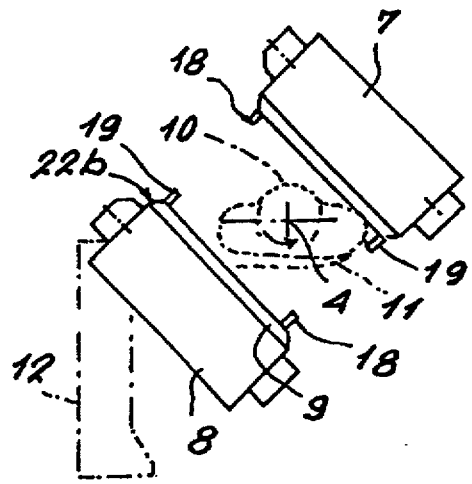
Figure 5:
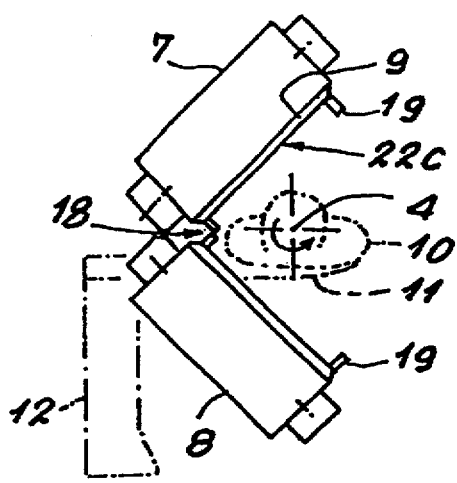

Thus, referring now to FIGS. 5a, 5b and 5c, it can be seen that the linear arrays 18, 19 must be located for certain examinations in parallel to the rotational axis 4 of the gamma camera 1, or else, for other examinations, orthogonally to this axis 4.

For example, for a full-body examination as shown in FIG. 5a, the linear arrays are positioned on the small sides of the collimator 9. The length of these linear arrays is then substantially equal to the width of the detector 7, 8. In this case, the linear arrays 18, 19 have curved ends 28 designed to prevent any contact between the patient's body 10 and the detectors 7, 8.

Furthermore, for a 180° tomographic examination as shown in FIG. 5b, the frame 22 is different and is positioned on the detector 7, 8 so that the linear arrays 18, 19 are located on the large sides of the collimator 9 in the direction of the length of the detector. In this case, the length of these linear arrays 18, 19 is substantially equal to the length of the detector 7, 8.

Similarly, for a 90° tomographic examination as shown in FIG. 5c, the frame 22 is positioned on the detector 7, 8 so that the linear arrays 18, 19 are located on the large sides of the collimator 9, in the lengthwise direction of said detector. Nevertheless, since the detectors 7, 8 are positioned at 90° with respect to each other, the collimators 9 are very close to each other by one of their large sides. This proximity makes it possible to minimize the blind region in which there is no efficient detection of the radioactivity given out by the patient 10. In this case, one of the linear arrays 18 has a limited height and has only one row of diodes or phototransistors. Consequently, in 90° tomography, it is possible to have only one safety plane. It is nevertheless also possible to produce three planes. In this case, these three planes are substantially parallel and secant by the single row of photodiodes (or phototransistors). The scanning and synchronization are then adapted to the fact that one and the same diode is selected thrice to correspond to three neighboring phototransistors.

In order to enable these different examinations to be made, according to the invention three different frames 22a, 22b, 22c having different sizes are available. One of these frames 22a is designed for examinations where the axis 4 is orthogonal to the bed 11, another frame 22b is designed for examinations where the axis 4 is parallel to the bed 11 and yet another frame 22c is designed for the 90° tomographic examination. These frames 22 are detachable. They may therefore be mounted or dismounted at will from the detectors 7, 8. For example, they may be clipped on to the detector 7, 8 or to the collimator 9 by means of clips or else they can be inserted along a groove of the detectors 7, 8 made for this purpose. According to yet another embodiment, the frames 22a, 22b, 22c may be positioned on the detector 7, 8 or the collimator 9 by means of through holes 25 in which there are inserted studs of said detector 7, 8 or of said collimator 9. A segment 27, by sliding, then provides for the locking or unlocking of the frame 22 in position. The mounting and dismounting are then done by hand. However, it is possible to conceive of a motor-driven system enabling, for example, a withdrawal of the linear arrays and their automatic positioning. Or again, the frames may be incorporated in collimators or even in a casing of the detector.

The electronic circuits used for the implementation of the invention are advantageously installed in the frame 22. Hence, the synchronizer, the infrared emission and reception circuits, the wires for the transmission of the signals from the synchronizer to said circuits and the electrical supply wires are positioned inside the frame 22 in the linear arrays 18, 19. Furthermore, the frame is supplied by the detector and there is a circuit to permit the movements of the detector when the frame is present.

What is claimed is:

1. A gamma camera comprising a frame, a base movable on the frame for rotation about a rotational axis and at least one arm movable with respect to said frame, capable of moving away radially with respect to the rotational axis and provided, at one free end, with a detector, said camera further comprising two approach planes substantially parallel to a plane of said detector so as to servo-control the relative position of one edge of a patient positioned between said two planes, and a safety plane positioned between the collimator and the two approach planes and substantially parallel to said collimator so as to define a limit position of the proximity of the patient wherein the planes are in the form of rows of light-emitting diodes positioned so as to face rows of photodetectors and further wherein a row of diodes of a plane is offset with respect to the perpendicular to diodes of a row of diodes of a neighboring plane.

2. A gamma camera according to claim 1, wherein the photodetectors are light-detecting phototransistors.

3. A gamma camera according to claim 1, comprising a synchronization circuit operatively connected such that emission of light by the diodes and reception of said light by the photodetectors are synchronized.

4. A gamma camera according to claim 1, comprising a circuit operatively connected such that emission of light by diodes is pulsed and so that a diode emits light when neighboring diodes do not emit light.

5. A gamma camera according to claim 1, wherein the diodes of all the planes are arranged quincunxially on a linear array.

6. A gamma camera according to claim 1, wherein the planes are produced by two linear arrays arranged so as to be facing each other, one array bearing all the diodes and the other bearing all the photodetectors.

7. A gamma camera according to claim 6, wherein the two arrays are fixed to a frame.

8. A gamma camera according to claim 7, wherein the frame is fixed to a collimator.

9. A gamma camera according to claim 7, wherein the frame is detachable.

10. A gamma camera according to claim 8, wherein the frame is detachable.

11. A gamma camera according to claim 3, wherein the diodes and phototransistors of the frame are connected to an electronic circuit in the frame and wherein the frame is supplied by a detector circuit and further including a circuit to permit movement of the detector when the frame is present.

12. A gamma camera according to claim 11, wherein said camera includes several frames so as to be suited to a variety to uses.

13. A gamma camera according to claim 1, comprising a synchronization circuit operatively connected such that emission of light by the diodes and reception of light by said detectors are synchronized.

14. A gamma camera according to claim 13, comprising a circuit operatively connected such that emission of light by diodes is pulsed and so that a diode emits light when neighboring diodes do not emit light.

15. A gamma camera according to claim 14, wherein a row of diodes of a plane is offset with respect to the perpendicular to diodes of a row of diodes of a neighboring plane.

16. A gamma camera according to claim 15, wherein the diodes of all planes are arranged quincunxially on a linear array.

17. A gamma camera according to claim 16, wherein the planes are produced by two linear arrays arranged so as to be facing each other, one array bearing all the diodes and the other bearing all the photodetectors.

18. A gamma camera according to claim 17, wherein the two arrays are fixed to a frame.

19. A gamma camera according to claim 18, wherein the frame is fixed to a collimator.

20. A gamma camera according to claim 18, wherein the frame is detachable.

21. A gamma camera according to claim 1, wherein said light-emitting diodes are spaced approximately one centimeter from each other in said rows.

22. A gamma camera according to claim 1, wherein said rows of light-emitting diodes and rows of photodetectors are arranged in linear arrays, respectively, said linear arrays having chamfered end portions.

23. A gamma camera according to claim 1, wherein said frame is detachable.

* * * * *